United States Patent [19]

Weilbacher et al.

[11] 4,366,711
[45] Jan. 4, 1983

[54] METHOD OF TESTING FUEL RODS FOR ASSEMBLIES FOR NUCLEAR REACTORS AND CORRESPONDING APPARATUS

[75] Inventors: Jean-Claude Weilbacher, Champagne-sur-Oise; Jean Marini, Marly-le-Roi; Alain Gravelle, Fontenay-aux-Roses, all of France

[73] Assignee: Framatome, Courbevoie, France

[21] Appl. No.: 142,370

[22] Filed: Apr. 17, 1980

[30] Foreign Application Priority Data

Apr. 20, 1979 [FR] France .................................. 79 09984

[51] Int. Cl.$^3$ ............................................. G01N 29/00
[52] U.S. Cl. ........................................ 73/590; 73/599; 376/252
[58] Field of Search ................. 73/590, 592, 599, 627, 73/628, 629, 622; 176/19 LD, 19 R, 80; 376/249, 252

[56] References Cited

U.S. PATENT DOCUMENTS 3,512,400  5/1970  Lynnworth ........................... 73/599
3,945,245  3/1976  Stehle et al. .......................... 73/590

FOREIGN PATENT DOCUMENTS 2642156  3/1978  Fed. Rep. of Germany ........ 176/19 LD Primary Examiner—Stephen A. Kreitman
Attorney, Agent, or Firm—Pollock, Vande Sande & Priddy

[57] ABSTRACT

A method of testing new fuel rods for assemblies for nuclear reactors.

Ultrasonic waves are transmitted in the canning tube of the fuel element disposed in the open, with an oblique incidence with respect to the axis of the tube, from one region of the side wall of the tube. By reflection at the walls of the canning tube, these waves produce plate waves or Lamb waves. These Lamb waves are picked up after a certain distance has been covered along the length of the canning tube and the attenuation undergone by these Lamb waves is measured. From this, by comparison with the attenuation results obtained at another part of the length of the tube or with a standard tube, data on the possible presence of moisture in the fuel rod is deduced. The invention particularly applies to the testing of fuel rods of assemblies for a pressurized water nuclear reactor.

7 Claims, 6 Drawing Figures

METHOD OF TESTING FUEL RODS FOR ASSEMBLIES FOR NUCLEAR REACTORS AND CORRESPONDING APPARATUS

FIELD OF THE INVENTION

The invention concerns a method of testing fuel rods for assemblies for nuclear reactors, obtained by introducing fuel into a tubular can, filling with a gas under pressure and sealing of this can, this method having the aim of detecting traces of moisture which may have been introduced into the rod during its manufacture. The invention also concerns an apparatus for implementing this method of testing fuel rods.

BACKGROUND

In the manufacture of fuel rods intended to form assemblies for nuclear reactors, for pressurized water nuclear reactors in particular, pellets of fuel are introduced into a metal tube called a can and this tube is sealed at each of its ends by plugs welded sealingly at the ends of the tube after the air inside the tube has been evacuated and helium under sufficient pressure has been introduced.

The sealed fuel rod thus contains an inert gas under pressure which remains inside the canning for the whole life of the fuel rod. The presence inside the fuel rod of materials which attack the nuclear fuel or the canning material or, furthermore, materials liable to undergo nuclear reactions leading to the production of dangerous radio-active products is thus avoided.

The fuel rods are assembled in the form of parallel bundles by means of connecting structures allowing the formation of assemblies which will be introduced into the core of the nuclear reactor. If moisture has been introduced inside the fuel rod during its manufacture, the canning of this rod is liable to be hydrided during the working of the reactor.

It is therefore extremely important to confirm that these rods do not contain the least trace of moisture or water before the fuel rods are assembled.

This testing must be carried out from outside a sealed fuel rod and must be conducted with very great sensitivity.

Known methods also exist which allow the detection, inside a fuel assembly, of defective fuel rods, i.e. whose canning has fissures which can cause radio-active products to issue into the cooling fluid of the nuclear reactor.

The detection and locating of these defective fuel rods inside assemblies allows them to be replaced and allows the assembly whose defective rods have been replaced to be then used.

To detect these defective fuel rods, methods have been proposed using the propagation of ultrasounds in the can of the fuel rod and the measurement of the attenuation of the ultrasounds which may arise from the presence of faults in the material of the canning. This testing is carried out on assemblies which have been in service in the core of the reactor for a certain period of operation and the faults detected by the attenuation of the ultrasounds are constituted by fractures in the can introducing a significant attenuation factor.

The introduction of cooling water inside the fuel rods also causes very considerable attenuation of the ultrasonic signal because of the relatively large quantities of water introduced into the fuel rod through the fissures in its canning.

A method of locating defective fuel rods is also known in which the cans of the fuel slugs are heated near one plug so that, when a defective rod is present, the moisture inside this rod is vaporized and causes bubbles of vapour or drops of condensation to form which can be detected at the level of the plug by means of an ultrasonic echo test.

In all these methods of detecting defective fuel rods inside assemblies which have been in service, the propagation of ultrasounds in the can of the fuel element is effected from an accessible region of the fuel rod in the assembly, i.e. from the plug of this fuel element or from the region immediately adjacent to the plug. In fact, the remainder of the fuel rod is not accessible in the assembly from which the end plates have been removed except where fuel rods disposed at the periphery of the assembly are concerned.

These tests must also be made on the assembly immersed inside the swimming pool of the reactor since we are concerned with an assembly which has remained in the core of the nuclear reactor for some time.

For all these reasons, the ultrasonic testing methods used hitherto for detecting fuel rods have not been transferable to testing for very slight traces of moisture in new fuel rods where the can has no fissures or other significant faults.

A method of testing steam generator tubes is also known, which uses the propagation of ultrasonic waves produced by the reflection of ultrasounds at the wall of these thin tubes, termed "plate waves" or "Lamb waves". These Lamb waves undergo attenuation when they encounter a fault such as a fissure or a saw cut in the tubular wall.

OBJECT OF THE INVENTION

The object of the invention is therefore to propose a method of testing new fuel rods for assemblies for nuclear reactors, obtained by introducing fuel into a tubular can, filling with gas under pressure and sealing of this can by plugs fixed sealingly to the can and constituting the ends of the fuel rod, for detecting traces of moisture which may have been introduced into the rod during its manufacture, this method having to allow extremely small quantities of moisture inside the rod to be detected and the whole length of this fuel rod to be explored.

SUMMARY OF THE INVENTION

With this object, to implement the method according to the invention, in the canning tube of the fuel element, disposed in the open, ultrasonic waves are transmitted with an oblique incidence with respect to the axis of the tube from one region of the side wall of the tube, these waves producing plate waves or Lamb waves by reflection at the walls of the canning tube; these Lamb waves are picked up after covering a certain distance along the length of the canning tube and the attenuation undergone by these Lamb waves is measured in order to deduce data therefrom on the possible presence of moisture in the fuel rod by comparison with the attenuation results obtained at another part of the length of the tube or from a standard tube.

BRIEF DESCRIPTION OF THE DRAWINGS

With the object of making the invention completely understood, several embodiments of the method according to the invention, using various arrangements of apparatuses for transmission and reception of ultrasonic waves, will now be described by way of non-limiting examples.

DETAILED DESCRIPTION

Figure 1:
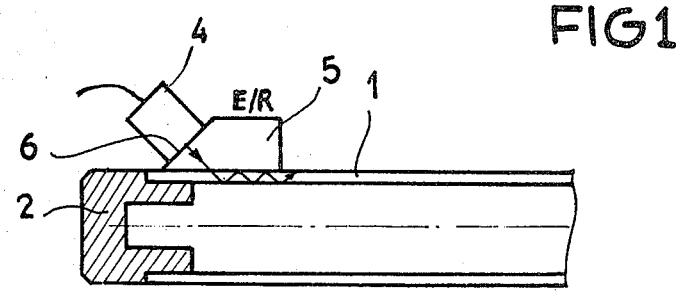
FIG. 1 represents, in a sectional view, the end of a fuel rod on which an ultrasonic transmitter-receiver apparatus has been placed to carry out the method according to the invention.

FIG. 1 shows the end of a fuel rod comprising a can 1 closed by a plug 2 welded on the end of the tubular can 1, the tubular can containing pellets of nuclear fuel which are not represented and helium ensuring a suitable pressurizing of the fuel rod.

The apparatus for transmitting and receiving ultrasounds comprises a transmitter-receiver 4 and a block 5 of Plexiglas coupled by its face 6 inclined at 45° with respect to the axis of the fuel rod to the transmitting and receiving face of the transducer 4.

The Plexiglas block ensures a good coupling between the transducer 4 and the canning tube 1 and presents a cylindrical recess in its supporting face in contact with the canning tube 1 to achieve this.

The ultrasonic waves transmitted by the transducer 4 are sent by means of the Plexiglas block into the canning tube 1 with an angle of incidence of 45° with respect to the axis of the tube.

In this way, the ultrasonic waves transmitted into the side wall of the canning tube 1 do not interfere with the plug 2 and, by reflection at the inner surface and the outer surface of the tube 1, give rise to plate waves or Lamb waves which are propagated in the axial direction of the tube over the whole side surface of this tube. The preferred mode generally produced is the mode $S_0$.

The transducer 4 and the block 5 are selected so as transmit and receive in a preferred way a mode of Lamb waves which allows a propagation in the tube with a slight attenuation and negligible parasitic signals in the case of a tube without fault and moisture.

Figure 2:
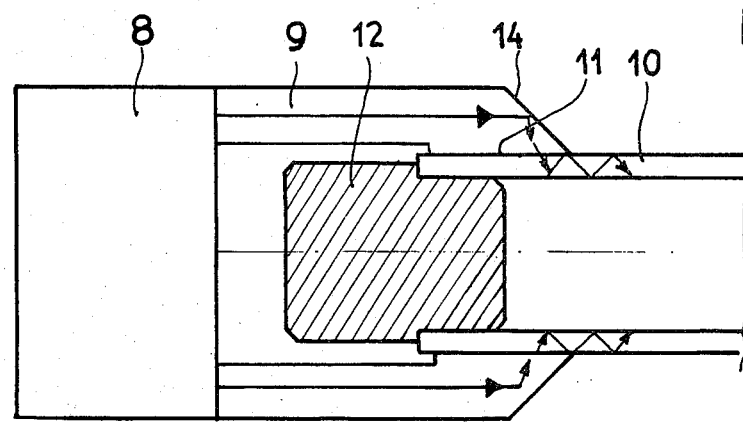
FIG. 2 represents on a larger scale and in a sectional view the region adjacent to the plug of a fuel rod on which an ultrasonic transmitter-receiver apparatus has been fitted, allowing use of the method according to the invention.

FIG. 2 shows an alternative form of the Plexiglas connecting piece allowing waves to be produced in the can of the fuel rod whose angle of incidence is in the region of 45°, this piece surrounding the outer surface of the can of the fuel rod at one of its ends.

In the arrangement represented in FIG. 2, the ultrasonic transmitter-receiver apparatus 8 is coupled to a connecting piece 9 whose contact face 11 surrounds the outer surface of the canning tube 10 on the part of it near the plug 12.

The ultrasonic waves reflected at the face 14 of the Plexiglas block 9 are reflected towards the side surface of the tube 10 so as to enter this tube with an incidence in the region of 45°. The waves reflected by the inner and outer surfaces of the tube 10 cause Lamb waves to propagate in the axial direction of the tube and undergo no reflection due to the plug 12 in the course of their propagation towards the opposite end of the canning tube.

In the case of the apparatuses represented in FIGS. 1 and 2, the transmission of Lamb waves and the propagation of these waves towards the end of the canning tube opposite the end represented in FIGS. 1 and 2 cause an echo when these Lamb waves are reflected by the plug at the opposite end to the plug 2 or the plug 12.

The transmitter-receiver apparatus 4 or 8 allows the echo signal to be picked up, and recorded, and the attenuation due to the distance covered in the tube to be measured.

In the case of the canning tube of new fuel rods, the attenuation is extremely slight in all cases of the tube containing no moisture, with the clear exception of cases when the canning tube happens to present a fissure arising from a fault in manufacturing and where the welding between the canning tube and the plug at which the reflection of waves occurs is defective.

In these particular instances, some idea of the origin of the attenuation of the signal can be obtained by analysing the signal received so as to detect the presence of parasitic signals.

If the attenuation is accompanied by the presence of a single parasitic signal, a fissure is present and the attenuation is at least partially due to this fissure.

If the presence of parasitic signals is not recorded, a welding fault, which is responsible for the attenuation of the echo signal, is then present.

In the case of new fuel rods, these faults are relatively rare and in almost all cases the attenuation of the signal received is due to the presence of traces of moisture in the tube.

This presence of moisture in the tube, in the form of very fine droplets hanging on the inner wall of the canning tube, causes the appearance of a series of parasitic signals characteristic of the presence of water in the canning tube.

Figure 3:
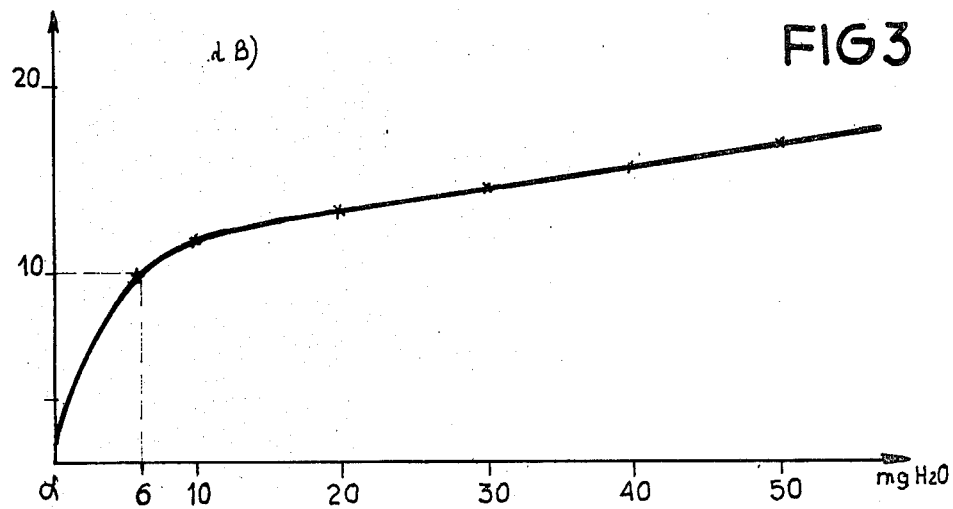
FIG. 3 represents variations in the attenuation of Lamb waves in the can of a fuel rod, as a function of the quantity of residual water inside the fuel rod.

The attenuation of the signal also allows the quantity of water in the tube to be ascertained when a curve like that represented in FIG. 3 has been traced. Such a curve is obtained by making measurements of attenuation on the standard canning tubes containing measured amounts of water and by noting them on a graph like that represented in FIG. 3.

This FIG. 3 shows that it is possible to measure amounts as low as 6 mg which would correspond to an attenuation of the echo which is easily measured, of the order of 10 decibels.

This result compares very favourably with the result of previous methods which were limited to a relatively low sensitivity since only the presence of amounts of water of the order of 50 g could be detected, approximately representing the quantity of water in a drop detectable by the ultrasonic methods of the prior art.

Figure 4:
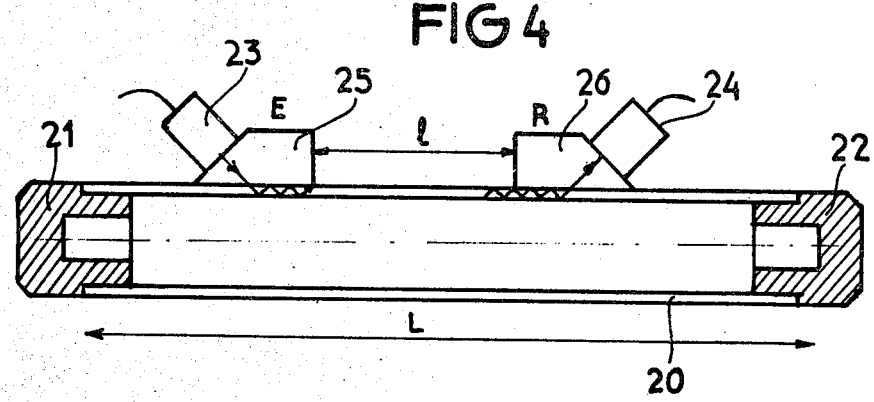
FIG. 4 represents, in a sectional view, a fuel rod on which two ultrasonic transmitter-receiver apparatuses have been mounted, one transmitting, the other receiving.

With reference to FIG. 4, a fuel rod is shown comprising a canning tube 20 and two end plugs 21 and 22 on the side surface of which have been placed two apparatuses 23 and 24 for transmitting and receiving ultrasounds coupled to Plexiglas blocks 25 and 26 surrounding the side surface of the fuel rod canning tube 20.

The apparatus 23, 25 is an ultrasonic wave transmitter apparatus and the apparatus 24, 26 is an apparatus for receiving these waves after a certain distance has been covered of length L inside the tubular wall of the can 20.

The distance L between the two transducers is clearly less than the length of the fuel rod so that it is possible to explore the whole surface of the fuel rod by moving the unit formed by the transmitter and receiver separated by a length L.

The ultrasonic transmitter and receiver can be made solid by means of a common support which allows the separation L of these two transducers to be maintained.

In the same way as when the apparatuses represented in FIGS. 1 and 2 are used, the attenuation of the Lamb waves produced in the tube by the ultrasonic waves incident with an angle in the region of 45° with respect to the axis of the tube, between the ultrasonic transmitter and receiver, is measured.

In the case of the detection of an attenuation of the Lamb waves, for one position of the transmitter and receiver, the presence of moisture on the inner side wall of the canning tube between the ultrasonic transmitter and receiver can be deduced from this.

By moving the apparatuses along the fuel rod, the results obtained at the various regions of the rod explored are easily compared and these results can easily be compared to detect an abnormal attenuation of the Lamb waves due to the presence of moisture in the tube.

This apparatus and this method of examination are particularly advantageous when defective rods are being tested so that they can be decanned and replaced. In fact, comparison of the results obtained at the various regions of the fuel rod is immediate and allows very rapid determination of an anomaly in the can of the fuel rod.

Figure 5:
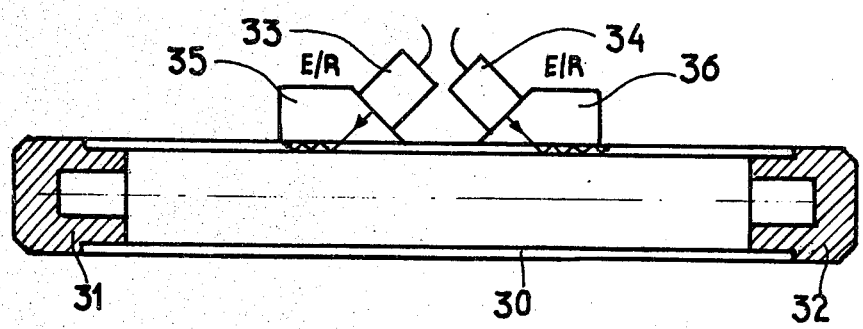
FIG. 5 represents, in a sectional view, a fuel rod on which two ultrasonic transmitter-receiver apparatuses have been mounted for using the method according to the invention.

With reference to FIG. 5, a new embodiment of an apparatus allowing implementation of the method according to the invention is shown in which the canning tube 30 of a fuel rod closed by two plugs 31 and 32 is covered by ultrasonic waves directed in opposite directions of propagation by means of two ultrasonic transmitter-receivers 33 and 34 connected to Plexiglas blocks 35 and 36, surrounding the outer surface of the tube and transmitting ultrasonic waves directed approximately at 45° with respect to the axis of the tube in symmetrical directions with respect to a transverse plane of the tube.

These Lamb waves are propagated in opposite directions and are simultaneously reflected by the plugs 31 and 32 and received on return by the transmitter-receivers 33 and 34 respectively.

In this way the signals corresponding to each of the two can-halves in which the ultrasounds are propagated are recorded simultaneously by means of a two-channel oscillograph, the transmitter-receiver apparatuses being disposed approximately at the middle of the tube 30.

In this way the echo signals obtained by reflection at the plugs 31 and 32 can be directly compared by bringing these echo signals into coincidence so as to compare their amplitudes.

It is thus extremely easy to detect the possible presence of water and to determine the can-half affected by moisture.

This method thus avoids the use of a preliminary calibration since it uses the direct comparison of the attenuations in the two parts of the can of the fuel rod in which the Lamb waves are simultaneously propagated.

This method also has the advantage of eliminating the influence of metallurgical or mechanical characteristics of the material constituting the can since the comparison is made on two parts of the same metal tube.

Precise positioning of the transducers is ensured by observing the echo signals obtained for each of these two transducers and by moving these transducers so as to bring the echo signals into coincidence, which allows comparison of the amplitudes.

Figure 6:
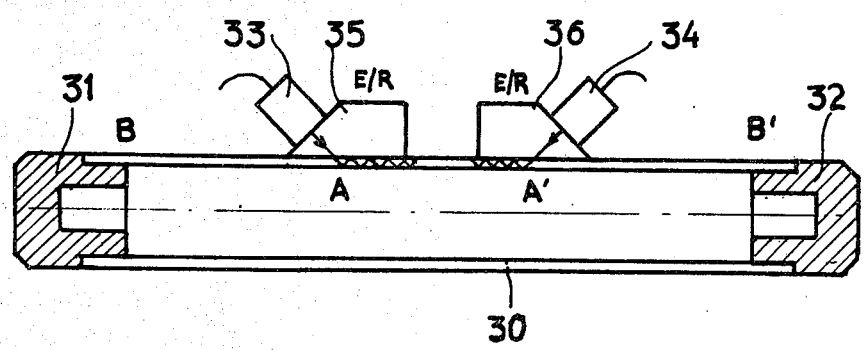
FIG. 6 represents a variant of the apparatus with two ultrasonic transmitter-receivers.

However, it is also possible to further improve the test method by using the apparatus represented in FIG. 6.

In fact, if the position of the transmitter-receivers 33 and 34 is reversed to obtain the arrangement represented in FIG. 6, the waves transmitted by the transducer 34 whose course in the tubular can begins at point A will cover the canning tube along the path A'BB'A.

The waves transmitted by the transmitter-receiver 33 will simultaneously cover the path AB'BA'.

Each of these courses represents an identical total path inside the canning tube and includes reflections at the plugs 31 and 32, so that there is thus a freedom from disturbances due to possible heterogeneities of the material of the tube and heterogeneities of the weldings of the two plugs.

Variations due to differences in the shape of the two plugs are also thereby eliminated.

In fact, if the signals transmitted and received by the two transmitter-receivers are recorded on an oscillograph, in the case of the tube containing no trace of water, the two records are absolutely identical since the two paths travelled are also identical.

In contrast, in the case of traces of water being present on the inner surface of the canning tube, the parasitic signals due to this water are detected with respect to the echo signals on both records. The echo signals are also attenuated which allows the amounts of water on the inner surface of the canning tube to be determined as previously. Two values of attenuation are clearly obtained which must be identical for both measurement paths.

It will be seen that, in all instances, the method according to the invention allows detection and quantitative determination of very slight traces of water inside the canning tube of a new fuel rod by a measurement using the propagation of ultrasonic waves in the side wall of the tube.

It will also be seen that the method according to the invention allows physical faults in the fuel rod (fissures or welding faults at the plugs) and traces of moisture to be easily perceived, after studying the signals picked up after a certain distance in the wall of the tube has been covered.

The method according to the invention clearly also allows the elimination of canning tubes with faults such as fissures or welding faults at the plugs.

Finally, comparative measurements on various portions of the canning tube allow the presence of moisture on these tube-portions to be determined very quickly.

But the invention is not limited to the embodiments just described; it also includes all the variants thereof, and modifications of points of detail are conceivable without thereby going beyond the scope of the invention.

Thus it is possible to use blocks of a material other than Plexiglas, the optimal angle of incidence of the waves being variable, however, as a function of the material selected.

The frequency of the waves transmitted can vary to a great extent though the applicant's trials have shown that the optimal frequencies of these waves are less than 1 MHz.

Some arrangements of transmitters or transmitter-receivers on the side surface of the canning tube have been described; apparatuses and types of comparative measurement other than those described are conceivable, however, by devising more or less complex courses for the Lamb waves in the wall of the canning tube, with or without reflection at the end plugs of the fuel rod or at other reflection apparatuses.

The method according to the invention and the corresponding apparatuses are moreover applicable not only in the case of fuel rods for assemblies intended to be placed in the core of pressurized water nuclear reactors but also to any type of fuel rod with a canning tube closed sealingly by plugs.

Lastly, the types of transducer described in FIGS. 4 to 6 can be advantageously replaced by an annular transducer structure entirely surrounding the tube, like that shown in FIG. 2.

We claim:

1. Method of testing new fuel rods for assemblies for nuclear reactors, obtained by introducing the fuel into a tubular can, filling with gas under pressure and sealing of this can by plugs fixed sealingly to the can and constituting the ends of the fuel rod, for detecting traces of moisture which may have been introduced into the rod during its manufacture, characterised by the fact that, in the canning tube of the fuel element disposed in the open, ultrasonic waves are transmitted with an oblique incidence with respect to the axis of the tube, from one region of the side wall of the tube, these waves producing, by reflection at the walls of the canning tube, plate waves or Lamb waves, that these Lamb waves are picked up after covering a certain distance along the length of the canning tube and that the attenuation undergone by these Lamb waves is measured in order to deduce data therefrom on the possible presence of moisture in the fuel rod by comparison with attenuation results obtained on another part of the length of the tube or on a standard tube.

2. Testing method according to claim 1, characterised by the fact that the signals transmitted are recorded so as to determine the possible presence of parasitic signals representative of the presence of fissures or traces of water.

3. Testing method according to claim 1, characterised by the fact that the attenuation measured is compared with attenuations measured in similar conditions in tubes containing known amounts of moisture so as to ascertain the amount of water contained in the tube.

4. Testing method according to any one of claims 1, 2 and 3, characterised by the fact that the course of the waves in the tube is in a direction between the point of incidence and one of the plugs of the fuel rod with return in the other direction and reception of the waves at the level of the point of incidence, after reflection at the plug of the fuel rod.

5. Testing method according to any one of claims 1, 2 and 3, characterised by the fact that the course of the waves is between two points of the side surface of the fuel element in one direction only, transmission of the ultrasonic waves occurring at one of the points and reception at the other point.

6. Testing method according to any one of claims 1, 2 and 3, characterised by the fact that the transmission of the ultrasonic waves is simultaneous at two different points of the side surface of the can of the fuel rod with propagation of the ultrasonic waves towards the end plugs of the fuel rod and return in the other direction of the ultrasonic waves to the point from which they were transmitted, the attenuations of the signal after passing through the tube along each of the two courses being compared to determine the presence of traces of moisture.

7. Testing method according to any one of claims 1, 2 and 3, characterised by the fact that the ultrasonic waves are transmitted simultaneously at two different points of the side surface of the fuel rod in opposite directions of movement and that they are reflected at the two plugs of the fuel rod successively before, for each of the trains of waves, being picked up at the point at which the other train of waves are transmitted.

* * * * *